US010087152B2

(12) United States Patent
Prasad et al.

(10) Patent No.: US 10,087,152 B2
(45) Date of Patent: Oct. 2, 2018

(54) PROCESS FOR PREPARING (E)-(5,6-DIHYDRO-1,4,2-DIOXAZIN-3-YL)(2-HYDROXYPHENYL)METHANONE O-METHYL OXIME

(71) Applicant: Arysta LifeScience Corporation, Tokyo (JP)

(72) Inventors: Vic Prasad, Leawood, KS (US); Cameron Gibb, Apex, NC (US); Christopher Lynn Larson, Cary, NC (US); A. Sai Srikanth, Kurnool (IN); Jivan Dhanraj Pawar, Bangalore (IN); Sankar Balakrishnan, Tamilnadu (IN); K. N. Ravikumar, Bangalore (IN); Avinash Shesharo Mane, Bangalore (IN); Sagi Sateesh, Andhra Pradesh (IN); Sampadarao Ananda Rao, Andhra Pradesh (IN)

(73) Assignee: Arysta LifeScience Corporation, Tokyo (JP)

( * ) Notice: Subject to any disclaimer, the term of this patent is extended or adjusted under 35 U.S.C. 154(b) by 0 days.

(21) Appl. No.: 15/578,044

(22) PCT Filed: May 10, 2016

(86) PCT No.: PCT/IB2016/000871
§ 371 (c)(1),
(2) Date: Nov. 29, 2017

(87) PCT Pub. No.: WO2016/193822
PCT Pub. Date: Dec. 8, 2016

(65) Prior Publication Data
US 2018/0148423 A1 May 31, 2018

Related U.S. Application Data

(60) Provisional application No. 62/168,196, filed on May 29, 2015.

(51) Int. Cl.
*C07D 273/01* (2006.01)
*C07D 413/12* (2006.01)
*C07D 307/82* (2006.01)

(52) U.S. Cl.
CPC ......... *C07D 273/01* (2013.01); *C07D 307/82* (2013.01); *C07D 413/12* (2013.01)

(58) Field of Classification Search
CPC .................................................. C07D 273/04
USPC .......................................................... 544/65
See application file for complete search history.

(56) References Cited

FOREIGN PATENT DOCUMENTS

| EP | 0846691 | 6/1998 |
|----|---------|--------|
| WO | 2006/021368 | 3/2006 |
| WO | 2015/006203 | 1/2015 |

Primary Examiner — Douglas M Willis
(74) Attorney, Agent, or Firm — Carmody Torrance Sandak & Hennessey LLP

(57) ABSTRACT

A process for preparing (E)-(5,6-dihydro-1,4,2-dioxazin-3-yl)(2-hydroxyphenyl)methanone O-methyl oxime is described which includes: (i) reacting benzofuran-3(2H)-one O-methyl oxime (1) with at least one nitrite selected from n-butyl nitrite and tert-butyl nitrite, in the presence of a metal alkoxide to form (2Z,3Z)-2,3-benzofuran-dione O3-methyl dioxime (2) as the predominant isomer; (ii) reacting the (2Z,3Z)-2,3-benzofuran-dione O-methyl dioxime (2) with 2-haloethanol to form (2Z,3Z)-benzofuran-2,3-dione 02-(2-hydroxyethyl) O3-methyl dioxime (3); and (iii) reacting the (2Z,3Z)-benzofuran-2,3-dione 02-(2-hydroxyethyl) &-methyl dioxime (3) with an acid to form (E)-(5,6-dihydro-1,4,2-dioxazin-3-yl)(2-hydroxyphenyl)methanone (9-methyl oxime (4);

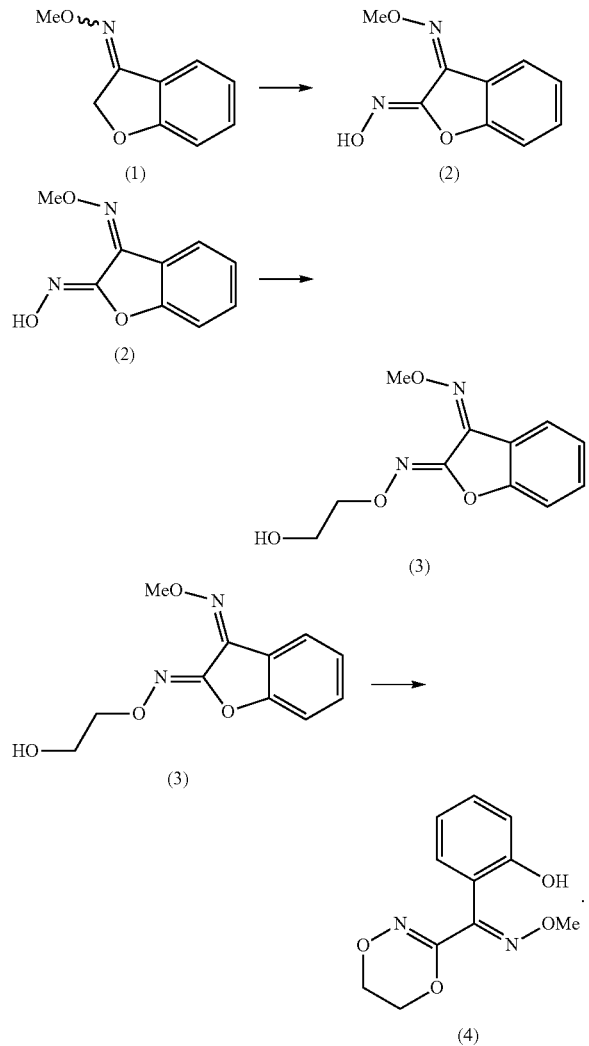

10 Claims, No Drawings

PROCESS FOR PREPARING (E)-(5,6-DIHYDRO-1,4,2-DIOXAZIN-3-YL)(2-HYDROXYPHENYL)METHANONE O-METHYL OXIME

TECHNICAL FIELD

The present disclosure provides an improved process of preparing (E)-(5,6-dihydro-1,4,2-dioxazin-3-yl)(2-hydroxyphenyl)methanone O-methyl oxime, an intermediate useful for the synthesis of fluoxastrobin.

BACKGROUND

Fluoxastrobin is a strobilurin-type fungicidal active ingredient used for controlling fungal diseases such as early blight, late blight, leaf spots, leaf rust, and *Rhizoctonia solani*. Fluoxastrobin has been registered for foliar use on peanuts, tuberous and corm vegetables, leaf petiole vegetables, fruiting vegetables, and turf, as well as seed treatment for potato, peanuts, and turf. Turf applications are labeled for professional pest control operators.

Bayer provides a number of synthetic pathways to fluoxastrobin, although all proceed through a consecutive reaction of 4,6-dichloro-5-fluoro-pyrimidine with 2-chlorophenol and (E)-(5,6-dihydro-1,4,2-dioxazin-3-yl)(2-hydroxyphenyl)methanone O-methyl oxime (4) as described in U.S. Pat. No. 6,734,304 and shown below:

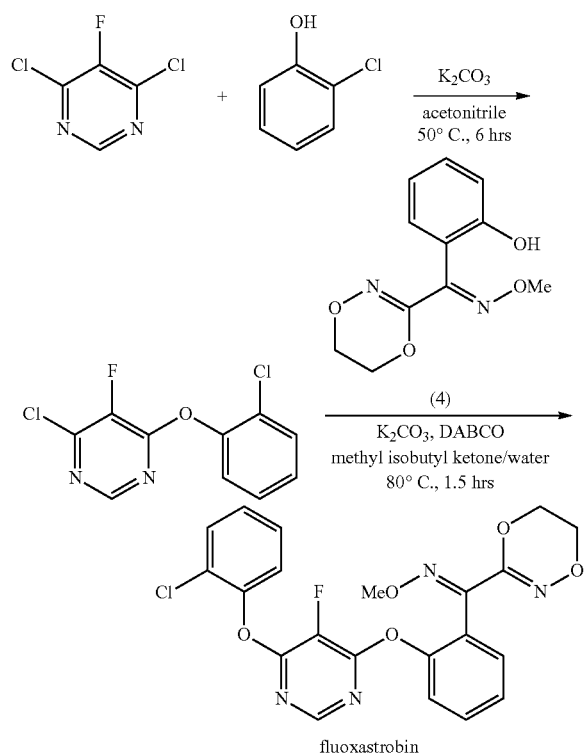

(E)-(5,6-dihydro-1,4,2-dioxazin-3-yl)(2-hydroxyphenyl)methanone O-methyl oxime (4) is an important intermediate in the synthesis of fluoxastrobin. However, known methods of synthesis of (E)-(5,6-dihydro-1,4,2-dioxazin-3-yl)(2-hydroxyphenyl)methanone O-methyl oxime are low yielding, include toxic reagents, and require lengthy and tedious work-up techniques and procedures, such as recrystallization and chromatography, which increase fluoxastrobin industrial production costs. Thus, there remains a need for a cost-efficient process of making (E)-(5,6-dihydro-1,4,2-dioxazin-3-yl)(2-hydroxyphenyl)methanone O-methyl oxime.

SUMMARY

The present disclosure provides a process of preparing (E)-(5,6-dihydro-1,4,2-dioxazin-3-yl)(2-hydroxyphenyl)methanone O-methyl oxime by:

(i) reacting benzofuran-3(2H)-one O-methyl oxime (1) with at least one nitrite selected from n-butyl nitrite and tert-butyl nitrite, in the presence of a metal alkoxide to form (2Z,3Z)-2,3-benzofuran-dione $O^3$-methyl dioxime (2) as the predominant isomer;

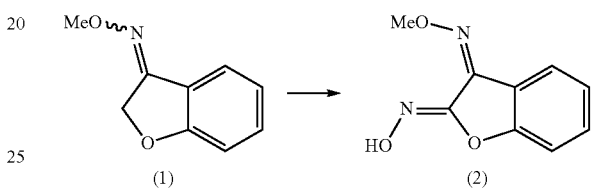

(ii) reacting the (2Z,3Z)-2,3-benzofuran-dione $O^3$-methyl dioxime (2) with 2-haloethanol to form (2Z,3Z)-benzofuran-2,3-dione $O^2$-(2-hydroxyethyl) $O^3$-methyl dioxime (3); and

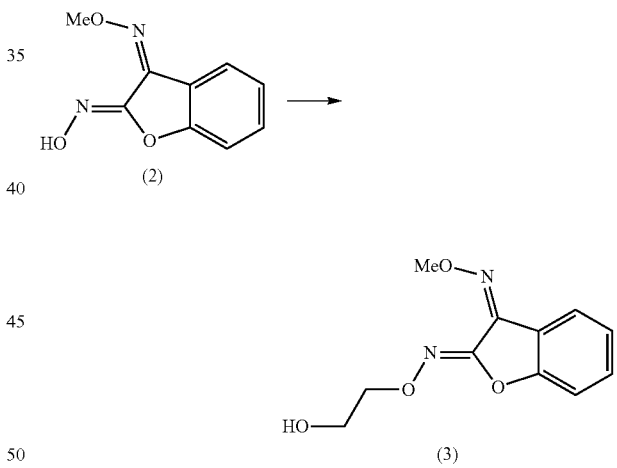

(iii) reacting the (2Z,3Z)-benzofuran-2,3-dione $O^2$-(2-hydroxyethyl) $O^3$-methyl dioxime (3) with an acid to form (E)-(5,6-dihydro-1,4,2-dioxazin-3-yl)(2-hydroxyphenyl)methanone O-methyl oxime (4)

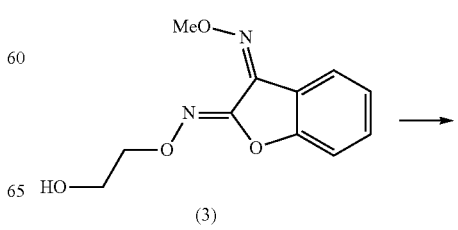

DETAILED DESCRIPTION

The disclosure includes the following embodiments, which should not be construed as limiting. Rather, these embodiments are exemplary and are provided to describe the invention to those skilled in the art. Like reference numerals refer to like elements throughout.

In an embodiment the disclosure includes a process for preparing (E)-(5,6-dihydro-1,4,2-dioxazin-3-yl)(2-hydroxyphenyl)methanone O-methyl oxime (1):

(i) reacting benzofuran-3(2H)-one O-methyl oxime (1) with at least one nitrite selected from n-butyl nitrite and tert-butyl nitrite, in the presence of a metal alkoxide to form (2Z,3Z)-2,3-benzofuran-dione $O^3$-methyl dioxime (2) as the predominant isomer;

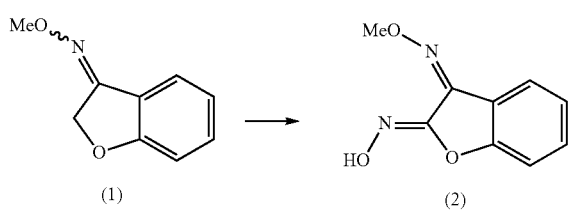 [SMILES: CON=C1COc2ccccc21 ; CO/N=C1\C(=N\O)Oc2ccccc21]

(ii) reacting the (2Z,3Z)-2,3-benzofuran-dione $O^3$-methyl dioxime (2) with 2-haloethanol to form (2Z,3Z)-benzofuran-2,3-dione $O^2$-(2-hydroxyethyl) $O^3$-methyl dioxime (3); and

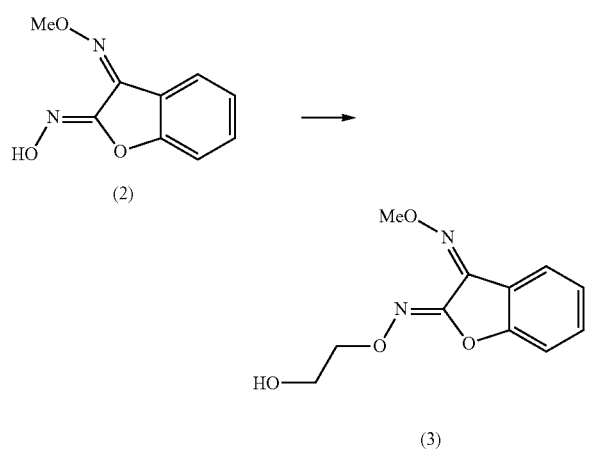

(iii) reacting the (2Z,3Z)-benzofuran-2,3-dione $O^2$-(2-hydroxyethyl) $O^3$-methyl dioxime (3) with an acid to form (E)-(5,6-dihydro-1,4,2-dioxazin-3-yl)(2-hydroxyphenyl)methanone O-methyl oxime (4);

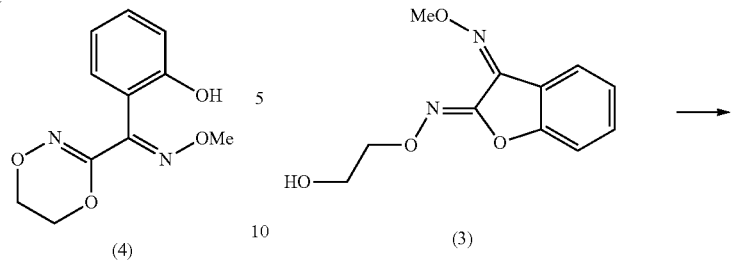

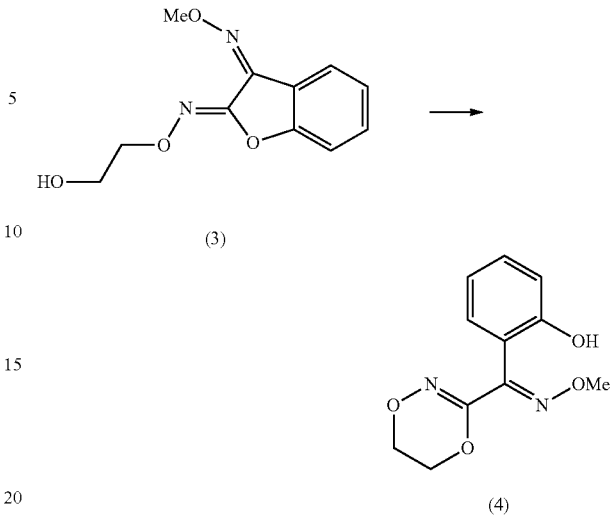

The initial step in the disclosed process is the reacting of benzofuran-3(2H)-one O-methyl oxime (1) with at least one nitrite selected from n-butyl nitrite and tert-butyl nitrite in the presence of a metal alkoxide to form (2Z,3Z)-2,3-benzofuran-dione $O^3$-methyl dioxime (2) as the predominant isomer.

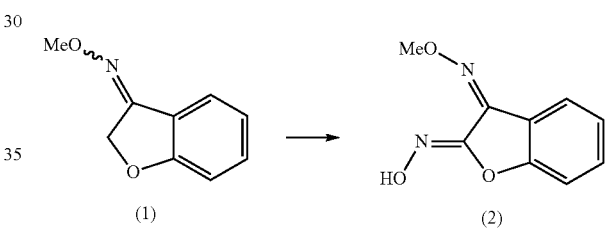

Generally, this reaction can be carried out by a number of nitrite reagents known in the art. However, it has been unexpectedly discovered that n-butyl nitrite $CH_3(CH_2)_3NO_2$ and tert-butyl nitrite $(CH_3)_3CNO_2$ are particularly useful for effecting the desired transformation. These reagents provide superior selectivity and better yields of (2Z,3Z)-2,3-benzofuran-dione $O^3$-methyl dioxime (2) compared to other nitrites. Indeed, the content of (2Z,3Z)-2,3-benzofuran-dione $O^3$-methyl dioxime (2) in a mixture of (3E)- and (3Z)-isomers is 94% to 98%. In addition, n-butyl nitrite and tert-butyl nitrite are substantially less toxic than many other alkyl nitrites (for example, methyl nitrite $CH_3NO_2$). Therefore, either n-butyl nitrite or tert-butyl nitrite (or both) can be safely used when it is desired to selectively prepare (2Z,3Z)-2,3-benzofuran-dione $O^3$-methyl dioxime (2) from benzofuran-3(2H)-one O-methyl oxime (1) on a large scale in a synthesis lab or an industrial setting.

The reaction of benzofuran-3(2H)-one O-methyl oxime (1) with at least one nitrite selected from n-butyl nitrite and tert-butyl nitrite is carried out in the presence of a solvent. Any solvent suitable to carry out the reaction can be used. However, the best results can be achieved by using an aprotic bipolar solvent, such as N,N-dimethylformamide ("DMF"), dimethylsulfoxide ("DMSO"), or N-methyl-2-pyrollidone ("NMP"), but is not limited thereto. For example, the reaction can be carried out by using N,N-dimethylformamide ("DMF").

The reaction of benzofuran-3 (2H)-one O-methyl oxime (1) with at least one nitrite selected from n-butyl nitrite and tert-butyl nitrite is carried out in the presence of a metal alkoxide. The metal alkoxide can be lithium alkoxide, sodium alkoxide, potassium alkoxide, rubidium alkoxide, cesium alkoxide or a combination thereof, but is not limited thereto. For example, the metal alkoxide can be sodium alkoxide, potassium alkoxide, or a combination thereof. Non-limiting examples of the sodium alkoxide include sodium methoxide ($NaOCH_3$) and sodium ethoxide ($NaOCH_2CH_3$). Non-limiting examples of the potassium alkoxide include potassium tert-butoxide ($KOC(CH_3)_3$).

The reaction typically starts by mixing a solution containing a nitrite reagent and metal alkoxide in a solvent with a solution of benzofuran-3(2H)-one O-methyl oxime (1). The mixing can take place at a temperature in a range of about 0° C. to about 25° C., for example, about 0° C. to about 5° C. After mixing, the reaction mixture is stirred at a temperature in a range of about 10° C. to about 50° C., for example, about 25° C. to complete the reaction.

When the reaction is carried out in the presence of n-butyl nitrite or tert-butyl nitrite the reaction produces one mole of n-butanol or tert-butanol for each mole of (2Z,3Z)-2,3-benzofuran-dione $O^3$-methyl dioxime (2). Typically, during the work up, the pH of the reaction mixture is adjusted by an acid (for example, by sulfuric acid or hydrochloric acid), and the precipitated product is filtered. The filtered product is washed with water to remove residual n-butanol or tert-butanol, unreacted metal alkoxide, impurities, and DMF. The product is then dried to remove residual water to give (2Z,3Z)-2,3-benzofuran-dione $O^3$-methyl dioxime (2) as a solid.

The next step in the disclosed process is the reaction of (2Z,3Z)-2,3-benzofuran-dione $O^3$-methyl dioxime (2) with 2-haloethanol to form (2Z,3Z)-benzofuran-2,3-dione $O^2$-(2-hydroxyethyl) $O^3$-methyl dioxime (3).

The reagent 2-haloethanol may include 2-chloroethanol, 2-bromoethanol, 2-iodoethanol, or a combination thereof. For example, the 2-haloethanol may be 2-chloroethanol. Alternatively, ethylene oxide can be used instead of 2-haloethanol in the reaction. However, 2-haloethanol is less toxic than ethylene oxide (which is a gas at ambient temperature) and can be easily manipulated on a large scale.

The reaction of (2Z,3Z)-2,3-benzofuran-dione $O^3$-methyl dioxime (2) with 2-haloethanol to form (2Z,3Z)-benzofuran-2,3-dione $O^2$-(2-hydroxyethyl) $O^3$-methyl dioxime (3) is conducted in the presence of a solvent. Any solvent suitable to carry out the reaction can be used. However, in certain embodiments an aprotic bipolar solvent, such as N,N-dimethylformamide ("DMF"), dimethylsulfoxide ("DMSO"), or N-methyl-2-pyrollidone ("NMP"), but is not limited thereto is used. For example, the reaction can be carried out using N,N-dimethylformamide ("DMF").

The reaction of (2Z,3Z)-2,3-benzofuran-dione $O^3$-methyl dioxime (2) with 2-haloethanol to form (2Z,3Z)-benzofuran-2,3-dione $O^2$-(2-hydroxyethyl) $O^3$-methyl dioxime (3) is conducted in the presence of a base. The base can be a metal carbonate, for example, lithium carbonate ($Li_2CO_3$), sodium carbonate ($Na_2CO_3$), potassium carbonate ($K_2CO_3$), cesium carbonate ($Cs_2CO_3$), but is not limited thereto. In an embodiment, the base can be potassium carbonate ($K_2CO_3$). When potassium carbonate is used as a base, the reaction produces one mole of potassium bicarbonate ($KHCO_3$) for each mole of the (2Z,3Z)-benzofuran-2,3-dione $O^2$-(2-hydroxyethyl) $O^3$-methyl dioxime (3) formed. The reaction is typically initiated by mixing (2Z,3Z)-2,3-benzofuran-dione $O^3$-methyl dioxime (2), 2-haloethanol, and the base in the solvent at a temperature in a range of about 0° C. to about 35° C., for example, about 20° C. to about 30° C. The reaction mixture can then be agitated at the temperature of reagent mixing to complete the reaction. However, to achieve a quicker conversion to the product, the reaction mixture is usually heated at a temperature in a range of about 50° C. to about 100° C., for example, about 75° C. to about 80° C. The reaction is typically quenched with water to precipitate the product from the solution. The product is then collected by filtration and washed with water to remove solvent (such as DMSO), salt (such as potassium bicarbonate), unreacted 2-haloethanol, and unreacted base (such as potassium carbonate). The filtered product is subsequently dried to remove residual water to give (2Z,3Z)-benzofuran-2,3-dione $O^2$-(2-hydroxyethyl) $O^3$-methyl dioxime (3) as a solid.

The next step in the disclosed process is the reaction of (2Z,3Z)-benzofuran-2,3-dione $O^2$-(2-hydroxyethyl) $O^3$-methyl dioxime (3) with an acid to form (E)-(5,6-dihydro-1,4,2-dioxazin-3-yl)(2-hydroxyphenyl)methanone O-methyl oxime (4):

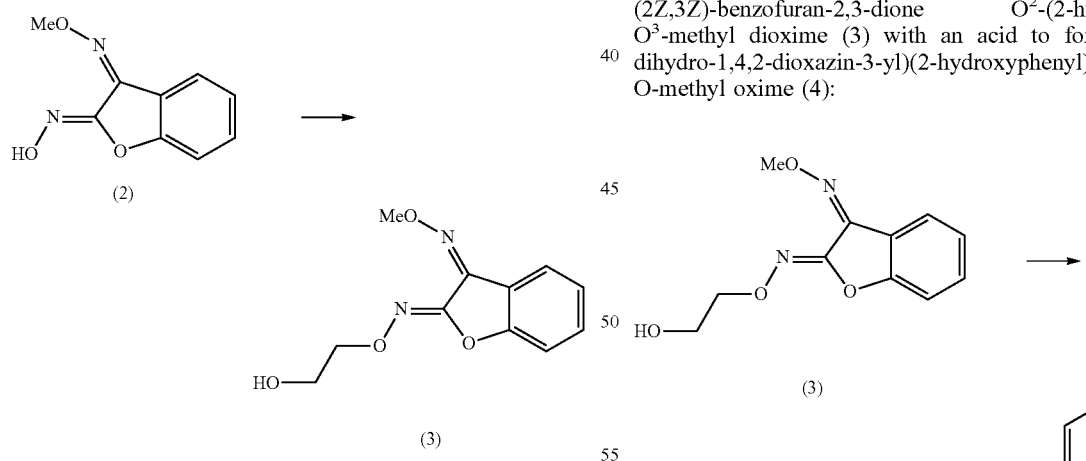

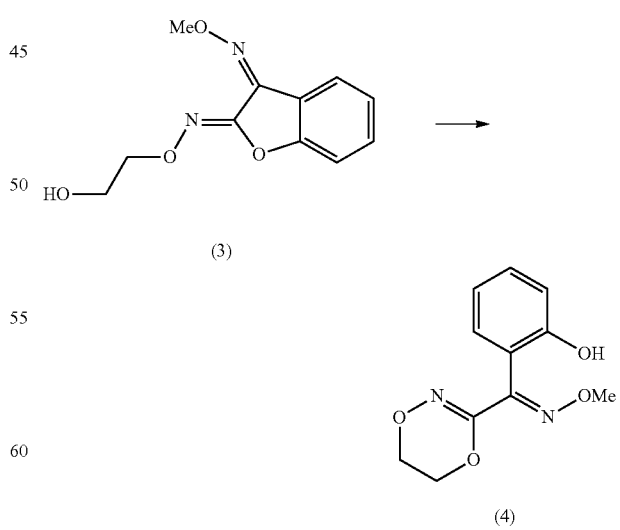

A selective conversion of (2Z,3Z)-benzofuran-2,3-dione $O^2$-(2-hydroxyethyl) $O^3$-methyl dioxime (3) to (E)-(5,6-dihydro-1,4,2-dioxazin-3-yl)(2-hydroxyphenyl)methanone O-methyl oxime (4) requires acid catalysis. It has been unexpectedly discovered that treatment of (2Z,3Z)-benzofuran-2,3-dione O$^2$-(2-hydroxyethyl) O$^3$-methyl dioxime (3) with an acid catalyst leads to highly preferential formation of (E)-(5,6-dihydro-1,4,2-dioxazin-3-yl)(2-hydroxyphenyl) methanone O-methyl oxime (4). In certain embodiments (E)-(5,6-dihydro-1,4,2-dioxazin-3-yl)(2-hydroxyphenyl) methanone O-methyl oxime (4) is formed exclusively, without any noticeable amount of the corresponding (Z)-isomer. Any acid suitable to carry out this transformation can be used. For example, the reaction can be carried out with hydrogen chloride (for example, hydrogen chloride gas), hydrogen bromide, sulfuric acid, methanesulfonic acid, trifluoromethanesulfonic acid, trifluoroacetic acid, or acetic acid. By using acid as a catalyst, (E)-(5,6-dihydro-1,4,2-dioxazin-3-yl)(2-hydroxyphenyl)methanone O-methyl oxime (4) is prepared in high isomeric purity and excellent yield. For example the ratio of (E)-(5,6-dihydro-1,4,2-dioxazin-3-yl)(2-hydroxyphenyl)methanone O-methyl oxime to (Z)-(5,6-dihydro-1,4,2-dioxazin-3-yl)(2-hydroxyphenyl) methanone O-methyl oxime may be greater than 85:1, 90:1, 92:1, 95:1, 98:1, or 99:1.

The reaction of (2Z,3Z)-benzofuran-2,3-dione O$^2$-(2-hydroxyethyl) O$^3$-methyl dioxime (3) to (E)-(5,6-dihydro-1,4, 2-dioxazin-3-yl)(2-hydroxyphenyl)methanone O-methyl oxime (4) is carried out in a solvent, which can be any solvent, stable to the action of an acid. For example, the reaction can be carried out in the presence of an ester solvent, such as ethyl acetate, propyl acetate, butyl acetate, but is not limited thereto. In an embodiment, the reaction can be carried out in the presence of butyl acetate. The reaction typically starts by contacting a solution of (2Z,3Z)-benzofuran-2,3-dione O$^2$-(2-hydroxyethyl) O$^3$-methyl dioxime (3) with an acid at a temperature in a range of about 0° C. to about 25° C., for example, about 0° C. to about 15° C. and maintaining that temperature for a period of about 1 hour to about 24 hours, for example, about 4 hours to about 6 hours until (2Z,3Z)-benzofuran-2,3-dione O$^2$-(2-hydroxyethyl) O$^3$-methyl dioxime (3) is consumed. Upon completion of the reaction, the mixture is typically diluted with water and the pH of the aqueous solution is adjusted to pH>12 with a base, for example, sodium hydroxide. The organic impurities are then removed by extraction with a solvent. The solvent used for the reaction can also be used for extraction. After extraction, the pH of the aqueous phase is lowered with an acid, for example, with acetic acid to crystallize (E)-(5,6-dihydro-1,4,2-dioxazin-3-yl)(2-hydroxyphenyl) methanone O-methyl oxime (4). The product is then collected by filtration and washed with water to remove salts and impurities. The filtered product is subsequently dried to remove residual water to give (E)-(5,6-dihydro-1,4,2-dioxazin-3-yl)(2-hydroxyphenyl)methanone O-methyl oxime (4) as a solid.

A distinguishing feature of the instantly disclosed process is that isolation of (2Z,3Z)-2,3-benzofuran-dione O$^3$-methyl dioxime (2), (2Z,3Z)-benzofuran-2,3-dione O$^2$-(2-hydroxyethyl) O$^3$-methyl dioxime (3), and (E)-(5,6-dihydro-1,4,2-dioxazin-3-yl)(2-hydroxyphenyl)methanone O-methyl oxime (4) is implemented by using simple filtration and does not require expensive, laborious, and time-consuming purification methods, such as recrystallization or chromatography. In addition, the isolation of (2Z,3Z)-2,3-benzofurandione O$^3$-methyl dioxime (2), (2Z,3Z)-benzofuran-2,3-dione O$^2$-(2-hydroxyethyl) O$^3$-methyl dioxime (3), and (E)-(5,6-dihydro-1,4,2-dioxazin-3-yl)(2-hydroxyphenyl) methanone O-methyl oxime (4) takes place at a temperature of 0° C. or greater, and does not require low-temperature cryogenic conditions. It is remarkable that the purity of the isolated (E)-(5,6-dihydro-1,4,2-dioxazin-3-yl)(2-hydroxyphenyl)methanone O-methyl oxime (4) is 99% or greater in certain embodiments. Thus, due to its efficiency, convenience, and low cost, the disclosed improved process of preparing (E)-(5,6-dihydro-1,4,2-dioxazin-3-yl)(2-hydroxyphenyl)methanone O-methyl oxime (4) is particularly valuable for industrial applications.

Methods of synthesis of benzofuran-3(2H)-one O-methyl oxime (1) are known in the art. For example, benzofuran-3(2H)-one O-methyl oxime (1) can be prepared as illustrated in Scheme 1.

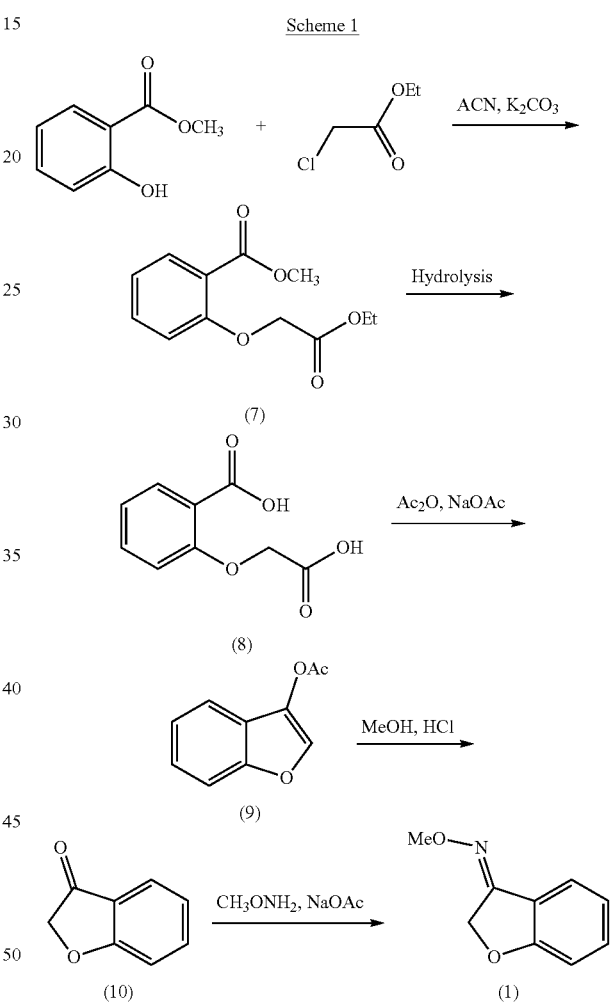

According to Scheme 1, methyl salicylate reacts with ethyl chloroacetate in the presence of potassium carbonate to give methyl 2-(2-ethoxy-2-oxoethoxy)benzoate (7). Hydrolysis of methyl 2-(2-ethoxy-2-oxoethoxy)benzoate (7) followed by a consecutive cyclization of 2-(carboxymethoxy) benzoic acid (8) with acetic anhydride in the presence of sodium acetate gives benzofuran-3-yl acetate (9) which is converted to benzofuran-3(2H)-one (10) by methanolysis. Treatment of benzofuran-3(2H)-one (9) with O-methylhydroxylamine and sodium acetate affords benzofuran-3(2H)-one O-methyl oxime (1).

As stated above, the oxime functionality of (E)-(5,6-dihydro-1,4,2-dioxazin-3-yl)(2-hydroxyphenyl)methanone O-methyl oxime (4) shares the same configuration as the oxime functionality of fluoxastrobin. This intermediate can be used to prepare fluoxastrobin as described below.

According to an embodiment, the disclosed process for preparing (E)-(5,6-dihydro-1,4,2-dioxazin-3-yl)(2-hydroxyphenyl)methanone O-methyl oxime (4) further comprises methods of preparing fluoxastrobin from the (E)-(5,6-dihydro-1,4,2-dioxazin-3-yl)(2-hydroxyphenyl)methanone O-methyl oxime (4).

For example the disclosure includes a method for preparing fluoxastrobin comprising:

(iv) reacting a 4,6-di-halo-5-fluoro-pyrimidine (5), wherein $X_1$ is halogen, with (E)-(5,6-dihydro-1,4,2-dioxazin-3-yl)(2-hydroxyphenyl)methanone O-methyl oxime (4), optionally in the presence of a first solvent and optionally in the presence of a base, to form a (E)-(2-((6-halo-5-fluoropyrimidin-4-yl)oxy)phenyl)(5,6-dihydro-1,4,2-dioxazin-3-yl)methanone O-methyl oxime (6):

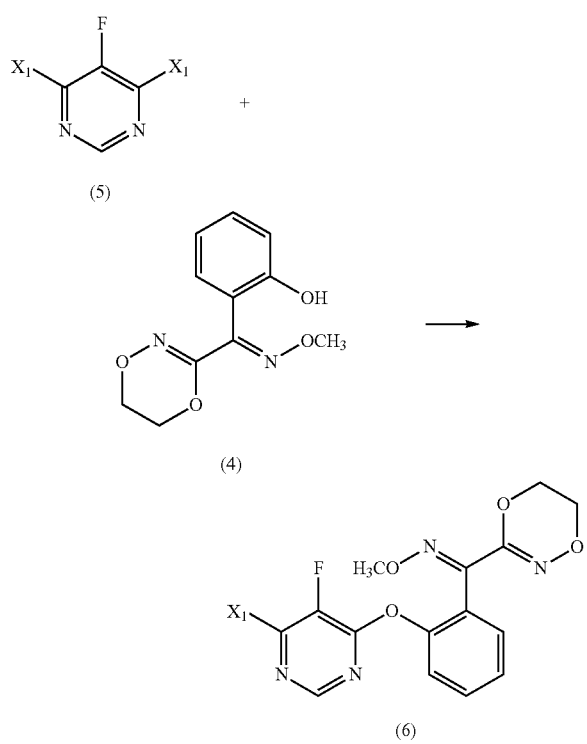

The step of reacting a 4,6-di-halo-5-fluoro-pyrimidine (5), wherein each $X_1$ is halogen, with (E)-(5,6-dihydro-1,4,2-dioxazin-3-yl)(2-hydroxyphenyl)methanone O-methyl oxime (4) may be carried out in the presence of a tertiary amine, for example, 1,4-diazabicyclo[2.2.2]octane ("DABCO"), 1,5-diazabicyclo[4.3.0]non-5-ene ("DBN"), or 1,8-diazabicyclo[5.4.0]undec-7-ene ("DBU"), and for example, 1,4-diazabicyclo[2.2.2]octane ("DABCO").

In an embodiment, an amount of 1,4-diazabicyclo[2.2.2]octane may be from about 0.02 moles to about 0.4 moles per mole of the (E)-(2-((6-halo-5-fluoropyrimidin-4-yl)oxy)phenyl)(5,6-dihydro-1,4,2-dioxazin-3-yl)methanone O-methyl oxime (4).

In another embodiment, the amount of 1,4-diazabicyclo[2.2.2]octane is from about 0.02 moles to about 0.2 moles per mole of the (E)-(2-((6-halo-5-fluoropyrimidin-4-yl)oxy)phenyl)(5,6-dihydro-1,4,2-dioxazin-3-yl)methanone O-methyl oxime (4).

(v) Step (iv) is followed by reacting the (E)-(2-((6-halo-5-fluoropyrimidin-4-yl)oxy)phenyl)(5,6-dihydro-1,4,2-dioxazin-3-yl)methanone O-methyl oxime (6) with 2-chlorophenol, optionally in the presence of a second solvent and optionally in the presence of a base, to form fluoxastrobin:

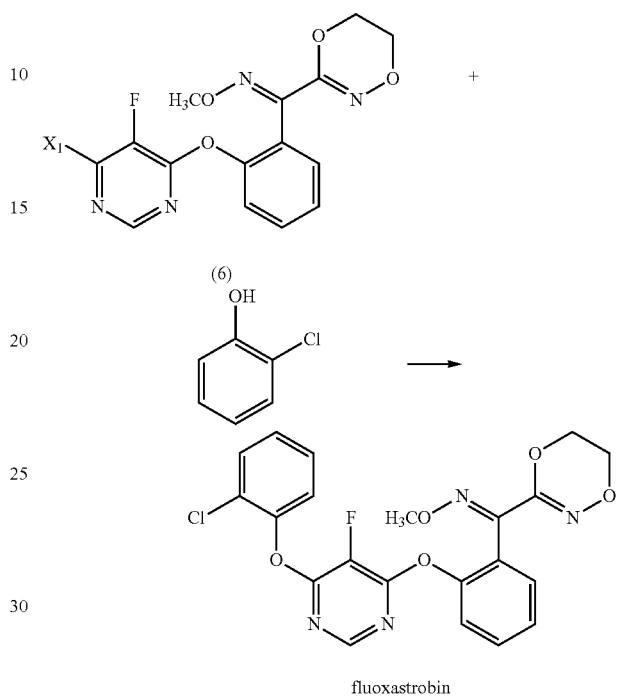

fluoxastrobin

The first and second solvent may be the same or different.

Steps (iv) and (v) in the process for preparing fluoxastrobin may be carried out as a one-pot process, i.e. without isolation and purification of intermediate (6). When steps (iv) and (v) are carried out as a one-pot process, the first and second solvents are necessarily the same.

In the step of reacting a 4,6-di-halo-5-fluoro-pyrimidine (5), wherein $X_1$ is halogen, with (E)-(5,6-dihydro-1,4,2-dioxazin-3-yl)(2-hydroxyphenyl)methanone O-methyl oxime (4), an amount of the 4,6-di-halo-5-fluoro-pyrimidine (5) may be from about 1 mole to about 4 moles per one mole of the (E)-(5,6-dihydro-1,4,2-dioxazin-3-yl)(2-hydroxyphenyl)methanone O-methyl oxime (4).

In the step of reacting of the (E)-(2-((6-halo-5-fluoropyrimidin-4-yl)oxy)phenyl)(5,6-dihydro-1,4,2-dioxazin-3-yl)methanone O-methyl oxime (6) with 2-chlorophenol, an amount of 2-chlorophenol may be from about 0.8 moles to about 4 moles per one mole of the (E)-(2-((6-halo-5-fluoropyrimidin-4-yl)oxy)phenyl)(5,6-dihydro-1,4,2-dioxazin-3-yl)methanone O-methyl oxime (6).

In the process for preparing fluoxastrobin, the step of reacting a 4,6-di-halo-5-fluoro-pyrimidine (5), wherein $X_1$ is halogen, with (E)-(5,6-dihydro-1,4,2-dioxazin-3-yl)(2-hydroxyphenyl)methanone O-methyl oxime (6) may be carried out at a temperature of about 0° C. to about 100° C., for example, about 40° C. to about 80° C. The reaction time may vary from about 1 hour to about 10 hours, for example, from about 1 hour to about 6 hours.

Alternatively fluoxastrobin may be prepared from (E)-(5,6-dihydro-1,4,2-dioxazin-3-yl)(2-hydroxyphenyl)methanone O-methyl oxime (4) by (iv) reacting a 4,6-di-halo-5-fluoro-pyrimidine (5), wherein $X_1$ is halogen, with 2-chlorophenol, optionally in the presence of a solvent and optionally in the presence of a base, to form a 4-halo-6-(2-chlorophenoxy)-5-fluoropyrimidine (11):

(v) and reacting the 4-halo-6-(2-chlorophenoxy)-5-fluoropyrimidine (11) with (E)-(5,6-dihydro-1,4,2-dioxazin-3-yl)(2-hydroxyphenyl)methanone O-methyl oxime (4), optionally in the presence of a solvent and optionally in the presence of a base, to form fluoxastrobin:

The solvent in steps (iv) and (v) for either method for preparing fluoxastrobin, can be a ketone solvent, for example, methyl iso-butyl ketone (MIBK). The base in steps (iv) and (v) of either method can be a metal carbonate, for example, potassium carbonate.

In these embodiments $X_1$ may be fluorine, chlorine, bromine, and iodine. For example, $X_1$ may be chlorine.

Steps (iv) and (v) of the process of either method for preparing fluoxastrobin may be carried out in the presence of a solvent. In an embodiment, the solvent may include a hydrocarbon solvent, a halogenated hydrocarbon solvent, an ether solvent, a ketone solvent, a nitrile solvent, an amide solvent, an ester solvent, a sulfoxide solvent, a sulfone solvent, water, or a combination thereof. The hydrocarbon solvent may include an aliphatic solvent, an alicyclic solvent, an aromatic solvent, or a combination thereof. Non-limiting examples of the hydrocarbon solvent include petroleum ether, pentane, hexane, heptane, cyclohexane, methylcyclohexane, benzene, toluene, 1,2-xylene, 1,3-xylene, 1,4-xylene, ethylbenzene, and cumene. Non-limiting examples of the halogenated solvent include chlorobenzene, dichlorobenzene, dichloromethane, chloroform, carbon tetrachloride, 1,1-dichloroethane, 1,2-dichloroethane, 1,1,1-trichloroethane, and 1,1,2-trichloroethane. Non-limiting examples of the ether solvent include diethyl ether, diisopropyl ether, methyl-tert-butyl ether, methyl-tert-amyl ether, 1,4-dioxane, tetrahydrofuran ("THF"), 2-methyltetrahydrofuran, 1,2dimethoxyethane ("DME"), and anisole. Non-limiting examples of the ketone solvent include acetone, 2-butanone, methyl isobutyl ketone, cyclopentanone, and cyclohexanone. In an embodiment, the ketone solvent may include methyl isobutyl ketone. Non-limiting examples of the nitrile solvent include acetonitrile ("ACN"), propionitrile, n-butyronitrile, iso-butyronitrile, and benzonitrile. Non-limiting examples of the amide solvent include N,N-dimethylformamide ("DMF"), N,N-dimethylacetamide ("DMA"), N-methylformamide, N-methylpyrrolidone ("NMP"), and hexamethylphosphoric triamide ("HMPA"). Non-limiting examples of the ester solvent include methyl acetate and ethyl acetate. Non-limiting example of the sulfoxide solvent include dimethyl sulfoxide ("DMSO"). Non-limiting example of the sulfone solvent include sulfolane.

In an embodiment, the solvent may be a mixture of the hydrocarbon solvent and the amide solvent.

For example, the solvent may be a mixture of the aromatic hydrocarbon solvent and the amide solvent. Non-limiting examples of the aromatic hydrocarbon solvent in this mixture may include benzene, toluene, 1,2-xylene, 1,3-xylene, 1,4-xylene, ethylbenzene, and cumene. Non-limiting examples of the amide solvent may include N,N-dimethylformamide ("DMF"), N,N-dimethylacetamide ("DME"), N-methylformamide, N-methylpyrrolidone ("NMP"), and hexamethylphosphoric triamide ("HMPA"). For example, the solvent may be a mixture of the aromatic hydrocarbon solvent such as any xylene or toluene and the amide solvent, which may be for example, N,N-dimethylformamide ("DMF"), N,N-dimethylacetamide ("DME"), N-methylformamide, N-methylpyrrolidone ("NMP"), or hexamethylphosphoric triamide ("HMPA"). For example, the solvent may be a mixture of the aromatic hydrocarbon solvent such as any xylene and the amide solvent, for example N,N-dimethylformamide ("DMF"), N,N-dimethylacetamide ("DME"), N-methylformamide, N-methylpyrrolidone ("NMP"), or hexamethylphosphoric triamide ("HMPA"). In another example, the solvent may be a mixture of the aromatic hydrocarbon solvent such as toluene and the amide solvent such as N,N-dimethylformamide ("DMF"), N,N- dimethylacetamide ("DME"), N-methylformamide,N-methylpyrrolidone ("NMP"), or hexamethylphosphoric triamide ("HMPA").

Furthermore, steps (iv) and (v) of either method for preparing fluoxastrobin may be carried out in the presence of a base. In an embodiment, the base may include an inorganic base, an organic base, or a combination thereof. The inorganic base may include a hydroxide, a hydride, an acetate, a carbonate, a bicarbonate, or a combination thereof. Non-limiting examples of the inorganic base include sodium hydroxide, potassium hydroxide, sodium hydride, potassium hydride, calcium hydride, sodium acetate, potassium acetate, sodium carbonate, potassium carbonate, rubidium carbonate, cesium carbonate, sodium bicarbonate, and potassium bicarbonate. Non-limiting examples of the organic base include trimethylamine, triethylamine, tributylamine, N,N-dimethylamine, N,N-di-iso-propylethylamine, N,N-dimethylbenzylamine, pyridine, 2-methylpyridine (2-picoline), 2,6-dimethylpyridine (2,6-lutidine), N-methylpiperidine, N-methylmorpholine ("NMM"), N,N-dimethylaminopyridine ("DMAP"), 1,5-diazobicyclo[4.3.0]non-5-ene ("DBN"), and 1,8-diazobicyclo[5.4.0]undec 7-ene ("DBU").

This invention is further illustrated by the following examples that are illustrative and should not be construed as limiting.

EXAMPLES

Methyl 2-(2-ethoxy-2-oxoethoxy)benzoate (7)

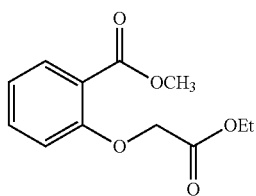

(7)

To a solution of ethyl salicylate (500 g, 3.288 mol) and $K_2CO_3$ (500 g, 1.1 equiv.) in DMF (2.0 L) is added ethyl chloroacetate (441.4 g, 1.1 equiv.) while the temperature is maintained below 30° C. The reaction mixture is heated to 60-65° C. for 18 hours. When the reaction is complete, the mixture is cooled to 20-30° C. and filtered. The collected solid is washed with DMF (2×500 mL) and dried by passing air for 15-30 min. The combined mother liquors are concentrated at 60-65° C. in vacuum, and the residue is further held under vacuum at 60-65° C. for 30-60 min to provide methyl 2-(2-ethoxy-2-oxoethoxy)benzoate (7) as a crude product (783 g, 100%) which is carried to the next step without further purification.

IR (cm-1) 2985.71m, 1725.89s, 1598.81s, 1489.10s, 1448.49s, 1378.78m, 1300.25m, 1250.90m, 1193.64s, 1136.53w, 1088.35s, 959.50w, 834.93w, 756.49s, 706.30w, 658.81w.

$^1$H NMR (400 MHz; CDCl$_3$) δ 1.306-1.271 (t, J=3.2 Hz, 3H), 3.906 (s, 3H), 4.292-4.238 (q, 2H), 4.713 (s, 2H), 6.897-6.877 (d, J=8 Hz, 1H), 7.068-7.028 (m, 1H,), 7.464-7.420 (m, 1H), 7.844-7.820 (dd, 1H, J=8 Hz).

HPLC Purity: 99%.

2-(Carboxymethoxy)benzoic acid (8)

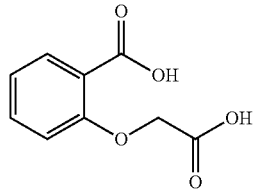

(8)

To a solution of NaOH (394.5 g, 3.0 equiv.) in $H_2O$ (3.12 L) is added 2-(2-ethoxy-2-oxoethoxy)benzoate (7) (783 g, 3.286 mol) while the temperature is maintained at 15-25° C. The reaction mixture is stirred and heated to 40° C. for 2 hours. When the reaction is complete, the mixture is diluted with $H_2O$ (295.5 g, 5 equiv.) and the pH is adjusted to 2-3 using concentrated $H_2SO_4$ (578 g, 1.76 equiv.) while maintaining the temperature at 15-25° C. The resultant mixture is stirred at 15-25° C. for 2 hours. The product is collected by filtration and washed with $H_2O$ (2×1.57 L). The product is dried by passing air at 20-30° C. for 60 min, and subsequently air dried at 70-85° C. until the moisture content is NMT 1.0% w/w to give 2-(carboxymethoxy)benzoic acid (8) (548 g, 85%) as a solid.

IR (KBr) (cm$^{-1}$) 3467.78w, 3178.72m, 2756.30w, 1743.43s, 1678.65s, 1367.36s, 1236.72s, 1056.69s.

$^1$H NMR (400 MHz; DMSO-d6) δ 4.734 (s, 2H), 6.975-6.954 (d, J=8.4 Hz, 1H), 7.008-6.954 (m, 1H), 7.457-7.413 (m, 1H), 7.633-7.610 (m, J=1.6 Hz, 1H), 12.791 (bs, 2H). MS (EI) m/z: 195.2 (M−1); MS (EI) (m/z): 195.2 (M−1), 137.2, 117, 97. HPLC Purity: 98%.

Benzofuran-3-yl acetate (9)

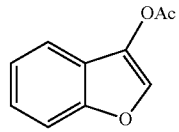

(9)

2-(Carboxymethoxy)benzoic acid (8) (548 g, 2.793 mol) is added to acetic anhydride (1,778 g, 6.23 equiv.) under stirring at 20-30° C. Pyridine (22.11 g, 0.1 equiv.) is added thereto, and the mixture is heated at reflux (130-140° C.) for 20 hours. When the reaction is complete, the mixture is cooled to 50-60° C. and concentrated by vacuum distillation. After distillation is complete, the residue is held under vacuum at 50-60° C. for 30 min to give crude benzofuran-3-yl acetate (9) (492 g, 100% yield) which is carried to the next step without further purification.

IR (cm$^{-1}$) 3060.43w, 1759.45s, 1577.24s, 1449.18s, 1361.45s, 1179.20s, 1090.38s, 890.75, 742.41.

$^1$H NMR (400 MHz; DMSO-d6) δ 2.384 (s, 3H), 7.332-7.292 (dd, 1H), 7.411-7.37 (dd, 1H), 7.62-7.576 (dd, J=9 Hz, 2H), 8.2 (s, 1H). GC-MS (EI) m/z: 176. HPLC Purity: 99%.

Benzofuran-3(2H)-one (10)

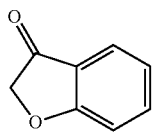
(10)

To a solution of benzofuran-3-yl acetate (9) (492 g, 2.792 mol) in methanol (1,915 mL) at 20-30° C. is added a solution of $H_2SO_4$ (98%, 346.6 g, 1.24 equiv.) in water $H_2O$ (2,266 g, 45 equiv.). The resultant mixture is heated at reflux (65-70° C.) for 3 hours. When the reaction is complete, the mixture is cooled to 5-10° C. and held at that temperature for 1 h to allow precipitation of the product. The product is collected by filtration and washed with $H_2O$ (3×1,644 mL) at 20-30° C. The collected product is then dried under vacuum at 20-30° C. to give benzofuran-3-one (307 g, 82%) as a solid.

IR (cm$^{-1}$) 2935.34, 1725.66, 1468.50, 1193.97.

$^1$H NMR (400 MHz; DMSO) δ 4.807 (s, 2H), 7.176-7.138 (t, 1H), 7.303-7.283 (d, J=8 Hz, 1H), 7.657-7.635 (m, 1H), 7.748-7.705 (m, 1H). GC-MS (EI) m/z: 134.13. M.P.: 101-103° C. HPLC Purity: 95%.

Benzofuran-3(2H)-one O-methyl oxime (1)

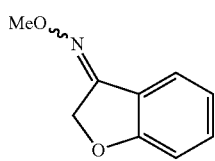
(1)

To a mixture of benzofuran-3-one (307 g, 2.288 mol), O-methyl-hydroxylamine hydrochloride (210.57 g, 1.1 equiv.) and sodium acetate (206.82 g, 1.1 equiv.) in dichloromethane (1,700 g, 1,282 mL) is slowly added acetic acid (128.17 g, 0.93 equiv.) while the temperature is maintained at 20-30° C. After addition, the batch is heated at reflux (40-45° C.) for 3 hours. When the reaction is complete, the mixture is cooled to 20-30° C. $H_2O$ (1,538 mL) is added and the resulting mixture is stirred at 20-30° C. for 10-15 min. When the mixture settles, the phases are separated and the organic layer is washed with $H_2O$ (1,538 mL). The organic phase is concentrated under vacuum at 20-40° C. After distillation is complete, the residue is kept under vacuum for 60 min at 40-45° C. to give crude benzofuran-3(2H)-one O-methyl oxime (1) as a mixture of isomers (355 g, 95%) which is carried to the next step without further purification.

IR (cm$^{-1}$) 3070.02, 2898.40, 1604.89s, 1398.80s, 1537.36, 1465.17, 1041.49, 985.45s, 747.70s, 628.55s, 554.54s.

$^1$H NMR (400 MHz; CDCl$_3$) δ 3.990 (s, 3H), 5.081 (s, 2H), 6.997-6.931 (m, 1H), 7.354-7.311 (m, 1H), 7.610-7.589 (m, J=7.8 Hz, 1H). MS (EI) m/z: 164 (M+1); MS (EI) m/z: 164 (M+1); 132.9. M.P.: 35-37° C. HPLC Purity: 99%.

(2Z,3Z)-benzofuran-2,3-dione O$^3$-methyl dioxime (2)

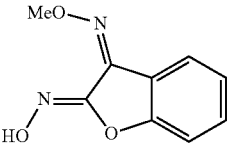
(2)

To a solution of sodium methoxide (176.36 g, 1.5 equiv.) in DMF (2,960 mL) is slowly added n-butyl nitrite (274.42 g, 1.1 equiv.) while the temperature is maintained at 0-5° C. Upon completion of the addition, the mixture is stirred at 0-5° C. for 10-15 min. A solution of benzofuran-3(2H)-one O-methyl oxime (1) (355 g, 2.177 mol) in DMF (355 mL) is slowly added to the reaction mixture while the temperature is maintained at 0-5° C. The resulting mixture is stirred at 0-5° C. for 30 min. The mixture is warmed to 20-30° C., stirred for 4 h until the reaction is complete, and then cooled to 0-10° C. $H_2O$ (7,105 mL) is added very slowly at 0-10° C. to quench the reaction. The pH of the mixture is adjusted to pH 1-2 using 50% aqueous $H_2SO_4$ (665.76 g, 1.56 equiv.) while the temperature is maintained at 0-5° C. The mixture is then stirred at 5-10° C. for 30 min. The product is collected by filtration, washed with $H_2O$ (4×1,420 mL) at 30° C., and dried under vacuum at 60-70° C. to give (2Z,3Z)-benzofuran 2,3-dione O$^3$-methyl dioxime (2) as a solid (310 g, 74%).

IR (cm$^{-1}$) 3243.39s, 3109.24m, 2935.39m, 2830.17m, 1599.15s.

$^1$H NMR (400 MHz; CDCl$_3$) δ 4.112 (s, 3H), 7.259-7.221 (m, J=7.6 Hz, 1H), 7.347-7.327 (d, J=8 Hz, 1H), 7.605-7.563 (m, 1H), 8.043-8.022 (m, J=7.6 Hz, 1H), 11.351 (s, 1H). MS (EI) m/z: 193.1 (M+1); MS (EI) (m/z): 193.1 (M+1), 195.3, 175.9, 162.1, 149.2. M.P: 180-182° C. HPLC Purity: 95%.

(2Z,3Z)-Benzofuran-2,3-dione O$^2$-(2-hydroxyethyl) O$^3$-methyl dioxime (3)

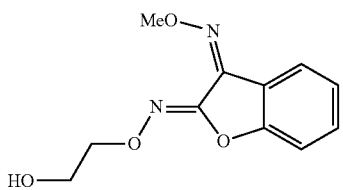
(3)

A mixture of (2Z,3Z)-benzofuran-2,3-dione O$^3$-methyl dioxime (2) (310 g, 1.611 mol), DMSO (930 mL), 2-chloroethanol (155.92 g, 1.2 equiv.) and potassium carbonate (311.28 g, 1.4 equiv.) is heated to 75-80° C. for 12 h until the reaction is complete. The reaction mixture is cooled to 20-30° C. The mixture is carefully poured into $H_2O$ (3,718 mL) while maintaining the temperature at 10-35° C. When the addition is complete, the resulting mixture is stirred at 10-20° C. for 45-60 min. The precipitated product is collected by filtration and washed with water (2×1,240 mL). The collected product is dried under vacuum on the filter for 1-2 h to give (2Z,3Z)-Benzofuran-2,3-dione O$^2$-(2-hydroxyethyl) O$^3$-methyl dioxime (3) (323.5 g, 85%) as a solid.

IR (cm$^{-1}$, KBr) 3434.29s, 3078.21w, 2939.71s, 2819.94w, 1594.86s, 1456.72s, 1345.45m, 1301.57w, 1064.99s, 933.28w, 868.16w.

$^1$H NMR (CDCl$_3$, 400 MHz) δ 2.126-2.140 (t, J=5.6 Hz, 1H), 3.974-3.980 (m, 2H), 4.220 (s, 3H), 4.379-4.389 (m, 2H), 7.162-7.196 (m, 2H), 7.448-7.487 (t, J=8 Hz, 1H), 8.056-8.076 (d, J=8 Hz, 1H).

$^{13}$C NMR (CDCl$_3$, 400 MHz) δ 59.534 (—CH$_2$—), 64.342, 77.543, 111.742, 118.106, 124.788, 128.187, 134.436, 142.573, 147.753, 157.036.

MS (EI) m/z 236.8 (M+1); MS2 (EI) m/z 237, 193.1, 162.0, 144.0 130.1, 119.1, 104.1, 90.0, 65.2. HPLC (Area %): 86%. M.P. 89-91° C.

(E)-(5,6-Dihydro-1,4,2-dioxazin-3-yl)(2-hydroxyphenyl)methanone O-methyl oxime (4)

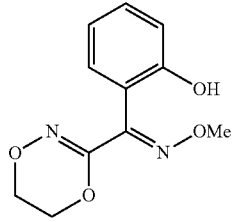

(4)

To butyl acetate (1,100 mL) cooled at 0-15° C. is added dry HCl (299.89 g, 6.0 equiv.) over 60 min. (2Z,3Z)-Benzofuran-2,3-dione O$^2$-(2-hydroxyethyl) O$^3$-methyl dioxime (3) (323.5 g, 1.369 mol) is added and the mixture is stirred at 0° C. for 4 hours. When the reaction is complete, the system is purged with nitrogen for 30 min and diluted with H$_2$O (970.57 mL). The pH of the reaction mixture is adjusted to pH>12 with an 11.13% solution of aqueous sodium hydroxide (2,461 g, 5.0 equiv.) while maintaining the temperature at 10-15° C. The reaction mixture is stirred for 15 min and the phases are separated. The product rich aqueous layer is washed with butyl acetate (2×1,470 mL) and the pH of the aqueous layer is adjusted to pH 5-5.5 using 50% aqueous acetic acid (323.5 g, 1.96 equiv.). The resultant mixture is cooled to 0° C. and stirred for 30 minutes to crystallize the product. The product is collected by filtration, washed with H$_2$O (647 mL), and dried under vacuum at 40° C. to give (E)-(5,6-Dihydro-1,4,2-dioxazin-3-yl)(2-hydroxyphenyl)methanone O-methyl oxime (4) as a crystalline solid (210 g, 65%).

$^1$H NMR (CDCl$_3$, 400 MHz) δ 3.960 (s, 3H), 4.149-4.169 (t, J=4 Hz, 2H), 4.411-4.431 (t, J=4 Hz, 2H), 6.844-6.907 (m, 4H), 7.270-7.313 (m, 1H), 7.367-7.390 (dd, J=1.2 Hz, J=1.6 Hz, 1H). HPLC (Area %): 99%. M.P. 110-114° C.

Diethyl 2-chloromalonate

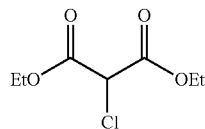

Preparation of diethyl 2-chloromalonate may be performed by methods known in the art, for example by the method of Babu, G. R. et al. (Der Pharma Chemica (2011) 3(6):437-442). Sulfuryl chloride is added to diethyl malonate at 60° C. The molar ratio of sulfuryl chloride to diethyl malonate is approximately 1.2:1. The generated HCl and SO$_2$ gases are vented to the scrubber as they are formed. The mixture is stirred for 6 h at 60° C. and concentrated under reduced pressure to give diethyl 2-chloromalonate as a residue, which is carried forward without further purification.

Diethyl 2-fluoromalonate

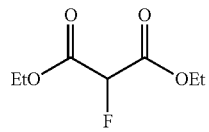

Diethyl 2-chloromalonate is added to the mixture of triethylammonium hydrofluoride and triethylamine at 80-90° C. under stirring. A molar excess of triethylammonium hydrofluoride and triethylamine to diethyl 2-chloromalonate is used. The resulting mixture is stirred at 100° C. for 18 hours. The mixture is cooled and diluted with water. The product is extracted with xylene. The phases are separated and the organic phase is concentrated to give diethyl 2-fluoromalonate as a residue, which is carried forward without further purification.

5-Fluoropyrimidine-4,6-diol

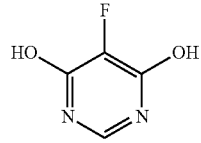

A solution of diethyl 2-fluoromalonate in formamide is added to a solution containing a molar excess of sodium methylate in methanol heated at 65° C. for more than 4 hours. When the reaction is complete, water is added. The mixture is acidified with hydrochloric acid to precipitate the product. The product is collected by filtration, washed with water and thoroughly dried to give 5-fluoropyrimidine-4,6-diol (75%) as a solid.

4,6-Dichloro-5-fluoropyrimidine

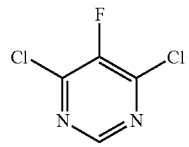

5-Fluoropyrimidine-4,6-diol is suspended in excess phosphorous oxychloride and the mixture is heated under stirring to 85° C. for 4 hours until production of hydrogen chloride stops. To this mixture, phosphorous trichloride is added over 15 min followed by an equimolar charge of chlorine gas over 1-2 hours. The mixture is heated to 105-108° C. and stirred until production of exhaust gases stops. The mixture is concentrated to a residue to remove excess $POCl_3$ at the pressure of 150-200 mbar. The residue is then distilled at 0.5 mbar pressure at approximately 40° C. to give 4,6-dichloro-5-fluoropyrimidine (82%) as a liquid.

4-Chloro-6-(2-chlorophenoxy)-5-fluoropyrimidine (11)

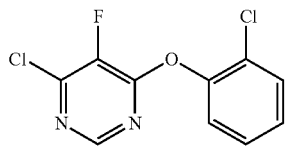

(11)

To a stirred mixture of methyl iso-butyl ketone (MIBK) (5,000 L), potassium carbonate (1,150 kg, 1.3 equiv.) and DCFP (1,067 kg, 6.39 kmol) heated at 65° C. is added 2-chlorophenol (825 kg, 1.003 equiv.) for 2 hours. During the addition, the temperature of the reaction mixture increases to 78° C. Stirring is continued at 78° C. for 4 hours. When the reaction is complete, water (4,000 L) is added to the hot mixture to dissolve the formed salts. After the phases are settled and separated, the lower salt phase is transferred to waste water pre-treatment by pressure hydrolysis. The remaining 4-chloro-6-(2-chlorophenoxy)-5-fluoropyrimidine (11) in MIBK is transferred to a storage tank for use in the final step.

Fluoxastrobin

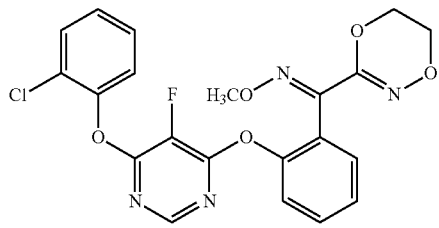 [SMILES: CO/N=C(/C1=NOCCO1)c1ccccc1Oc1ncnc(Oc2ccccc2Cl)c1F]

A solution of (E)-(5,6-Dihydro-1,4,2-dioxazin-3-yl)(2-hydroxyphenyl)methanone O-methyl oxime (4) (800 kg, 3.38 kmol) and DABCO (16 kg, 0.142 kmol, 0.042 equiv.) in water (650 kg) is added to a solution of 4-chloro-6-(2-chlorophenoxy)-5-fluoropyrimidine (11) in MIBK (3,176 kg, ca. 28% by weight, 3.43 kmol, 1.015 equiv.). To this mixture, potassium carbonate (625 kg, 1.34 equiv.) is added. The mixture is heated to 70° C. for 3 hours. Water (ca. 2,500 kg) is added to the hot mixture to dissolve all formed salts. The phases are settled and separated. The lower salt phase is transferred to waste water pretreatment by pressure hydrolysis. The organic product phase is distilled until about ⅓ of its original volume. The mixture is cooled to 20° C. Methanol is added to precipitate the product. The suspension is cooled to 5° C., filtered, washed with methanol and dried to give fluoxastrobin (1,430 kg, 92% over 2 steps).

IR $(cm^{-1}$, KBr) 3072.99w, 2981.58w, 2936.76s, 2819.79w, 2502.01w, 1601.14s, 1572.37s, 1447.88s, 1305.43m, 1268.11m, 1217.15m, 1191.21m, 1092.60m, 1049.05m, 1001.26w, 910.25w, 762.81w.

$^1$H NMR ($CDCl_3$, 400 MHz) δ 3.846 (s, 3H), 4.170-4.160 (t, J=4 Hz, 2H), 4.464-4.484 (t, J=4 Hz, 2H), 7.261-7.295 (m, 2H), 7.322-7.409 (2, 4H), 8.069 (s, 1H). $^{13}$C NMR ($CDCl_3$, 400 MHz) δ 63.103, 64.153, 64.550, 122.659, 123.259, 123.823, 125.712, 127.150, 127.397, 128.094, 130.511, 130.679, 130.776, 131.473, 134.138, 146.004, 148.166, 148.943, 150.354, 150.478, 151.819, 157.395, 157.466, 157.783, 157.854.

MS (EI) m/z 459.1 (M+1); MS2 (EI) m/z 427.1, 383.0, 366.9, 342.1, 306.2, 246.0, 231.1, 188.0. HPLC (Area %): 99.40%. M.P. 108-112° C.

The present disclosure is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

The terms "a" and "an" do not denote a limitation of quantity, but rather denote the presence of at least one of the referenced item. The term "or" means "and/or." The open -ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

As used herein, the term "halogen" refers to fluorine, chlorine, bromine, or iodine.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A process for preparing (E)-(5,6-dihydro-1,4,2-dioxazin-3-yl)(2-hydroxyphenyl)methanone O-methyl oxime of the formula (4):

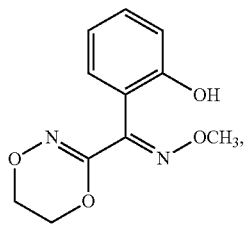

(4)

wherein the process comprises the following steps:
(i) reacting benzofuran-3(2H)-one O-methyl oxime of the formula (1):

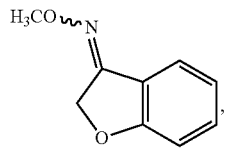

(1)

with at least one nitrite selected from the group consisting of n-butyl nitrite and tert-butyl nitrite, in the presence of a metal alkoxide, to provide a composition consisting of (2Z,3Z)-benzofuran-2,3-dione O³-methyl dioxime of the formula (2) and (2Z,3Z)-benzofuran-2,3-dione O³-methyl dioxime of the formula (2):

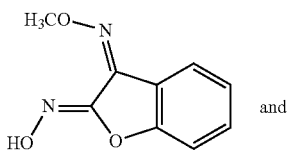

and

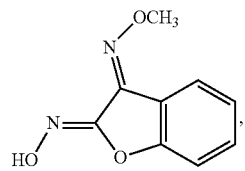

(2)

wherein (2Z,3Z)-benzofuran-2,3-dione O³-methyl dioxime of the formula (2) is the predominant stereoisomer;
(ii) reacting (2Z,3Z)-benzofuran-2,3-dione O³-methyl dioxime of the formula (2) with 2-haloethanol to provide (2Z,3Z)-benzofuran-2,3-dione O²-(2-hydroxyethyl) O³-methyl dioxime of the formula (3):

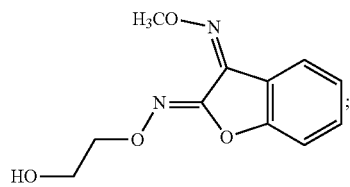

(3)

and
(iii) reacting (2Z,3Z)-benzofuran-2,3-dione O²-(2-hydroxyethyl) O³-methyl dioxime of the formula (3) above with an acid to provide (E)-(5,6-dihydro-1,4,2-dioxazin-3-yl)(2-hydroxyphenyl)methanone O-methyl oxime of the formula (4) above.

2. The process of claim 1, wherein the process further comprises independently isolating (2Z,3Z)-benzofuran-2,3-dione O³-methyl dioxime of the formula (2), (2Z,3Z)-benzofuran-2,3-dione O²-(2-hydroxyethyl) O³-methyl dioxime of the formula (3), and (E)-(5,6-dihydro-1,4,2-dioxazin-3-yl)(2-hydroxyphenyl)methanone O-methyl oxime of the formula (4); and
wherein the isolation of (2Z,3Z )-benzofuran-2,3-dione O³-methyl dioxime of the formula (2), (2Z,3Z)-benzofuran-2,3-dione O²-(2-hydroxyethyl) O³-methyl dioxime of the formula (3), and (E)-(5,6-dihydro-1,4,2-dioxazin-3-yl)(2-hydroxyphenyl)methanone O-methyl oxime of the formula (4) does not comprise recrystallization or chromatography, and
wherein the purity of the isolated (E)-(5,6-dihydro-1,4,2-dioxazin-3-yl)(2-hydroxyphenyl)methanone O-methyl oxime of the formula (4) is greater than or equal to 99%.

3. The process of claim 2, wherein the isolation of (2Z,3Z)-benzofuran-2,3-dione O³-methyl dioxime of the formula (2), (2Z,3Z)-benzofuran-2,3-dione O²-(2-hydroxyethyl) O³-methyl dioxime of the formula (3), and (E)-(5,6-dihydro-1,4,2-dioxazin-3-yl)(2-hydroxyphenyl)methanone O-methyl oxime of the formula (4) occurs at a temperature greater than or equal to 0° C.

4. The process of claim 1, wherein the process further comprises reacting benzofuran-3(2H)-one O-methyl oxime of the formula(1) with at least one nitrite in the presence of a bipolar aprotic solvent, or reacting (2Z,3Z)-benzofuran-2,3-dione O³-methyl dioxime of the formula (2) with 2-haloethanol in the presence of a bipolar aprotic solvent.

5. The process of claim 4, wherein the bipolar aprotic solvent is selected from the group consisting of N,N-dimethylformamide, N-methyl-2-pyrrolidone, and dimethylsulfoxide, and combination of one or more of the foregoing.

6. The process of claim 1, wherein the process further comprises reacting (2Z,3Z)-benzofuran-2,3-dione $O^2$-(2-hydroxyethyl) $O^3$-methyl dioxime of the formula (3) with an acid is carried out in an ester solvent.

7. The process of claim 6, wherein the ester solvent is n-butyl acetate.

8. The process of claim 1, wherein (2Z,3Z)-benzofuran-2,3-dione $O^3$-methyl dioxime of the formula (2) is present in the composition consisting of(2Z,3Z)-benzofuran-2,3-dione $O^3$-methyl dioxime of the formula (2) and (2Z,3Z)-benzofuran-2,3-dione $O^3$-methyl dioxime of the formula (2)in a range of 94% to 98%.

9. The process of claim 1, wherein the acid is hydrochloric acid.

10. The process of claim 1, wherein the metal alkoxide is selected from the group consisting of sodium alkoxide, and potassium alkoxide, and a combination of the foregoing.

* * * * *